(12) United States Patent
White et al.

(10) Patent No.: US 7,444,012 B2
(45) Date of Patent: Oct. 28, 2008

(54) METHOD AND APPARATUS FOR PERFORMING FAILURE ANALYSIS WITH FLUORESCENCE INKS

(75) Inventors: Jerry L. White, Glendale, AZ (US); Russell T. Lee, Phoenix, AZ (US)

(73) Assignee: Freescale Semiconductor, Inc., Austin, TX (US)

( * ) Notice: Subject to any disclaimer, the term of this patent is extended or adjusted under 35 U.S.C. 154(b) by 1088 days.

(21) Appl. No.: 10/626,781

(22) Filed: Jul. 24, 2003

(65) Prior Publication Data

US 2005/0018898 A1  Jan. 27, 2005

(51) Int. Cl.
*G06K 9/00* (2006.01)

(52) U.S. Cl. .................................. 382/149; 438/15
(58) Field of Classification Search ................. None
See application file for complete search history.

(56) References Cited

U.S. PATENT DOCUMENTS

| | | | | |
|---|---|---|---|---|
| 2,806,959 | A | * | 9/1957 | De Forest et al. ........... 250/302 |
| 5,592,571 | A | | 1/1997 | Peters |
| 5,715,334 | A | | 2/1998 | Peters |
| 5,761,337 | A | * | 6/1998 | Nishimura et al. ......... 382/150 |
| 6,324,298 | B1 | | 11/2001 | O'Dell et al. |
| 6,337,472 | B1 | | 1/2002 | Garner et al. |
| 6,342,400 | B1 | * | 1/2002 | DePetrillo ................... 438/15 |
| 6,781,232 | B2 | * | 8/2004 | Rubin ......................... 257/707 |
| 2002/0125136 | A1 | | 9/2002 | Sharaf et al. |

FOREIGN PATENT DOCUMENTS

| | | |
|---|---|---|
| EP | 0 855 022 B1 | 12/2002 |
| WO | WO 00/04488 | 1/2000 |

OTHER PUBLICATIONS

Braekvelt, "Metallographic Preparation of Steel Cord Cable Sections," *Struers Journal of Materialography*, 2003, 4 pgs.

* cited by examiner

*Primary Examiner*—Matthew C Bella
*Assistant Examiner*—Alex Liew
(74) *Attorney, Agent, or Firm*—Michael J. Balconi-Lamica

(57) ABSTRACT

A method for performing failure analysis on a semiconductor device under inspection includes preparing of a device sample using an encapsulation material containing a dye, the prepared device sample possibly including a failure area having wicked in encapsulation material containing the dye. The prepared device sample is then sectioned to facilitate viewing a cross section face of the device under inspection. Lastly, a dark field analysis on the prepared device sample is performed with the use of dark field illumination. Responsive to at least one failure area containing wicked in encapsulation material with dye occurring on the cross section face of the device under inspection, the failure area can be readily identified as well as a contrast and perspective of remaining portions of the cross section face being maintained.

21 Claims, 3 Drawing Sheets

METHOD AND APPARATUS FOR PERFORMING FAILURE ANALYSIS WITH FLUORESCENCE INKS

BACKGROUND

1. Field of the Invention

The present disclosure relates to semiconductor devices, and more particularly, to a method and apparatus for performing failure analysis of semiconductor devices with fluorescence inks.

2. The Related Art

Determining a point of failure in wafer level chip scale packages (WL-CSP's), or in product assembled to organic media, can be difficult. The point of failure may be due to either cracks in solder bumps, delamination of various organic films such as polyimide, bi-cycle butane (BCB), stress compensation layers (SCL) or soldermasks. Current cross sectioning techniques do no allow sufficient contrast to determine such a point of failure.

As known in the art, fluorescence microscopy is performed at narrow emission and excitation wavelengths, usually confined to medical and biological applications. Other reported work is in the field of metallography in the determination of metal porosity. In the preceding case, the technique lacks sufficient contrast to determine a point of failure in a wafer level chip scale package.

Fluorescent microscope technology requires costly specialized filter sets, for example, on the order of greater than $1,500.00 per set. Fluorescent microscope technology also requires high intensity light sources, for example, on the order of greater than 250 W. Furthermore, fluorescent microscope technology used in failure analysis suffers from loss of contrast between a failed area and a remaining section of the device under inspection. In addition, light from a 250 W source, for example, impinging upon a filter cube may only provide on the order of 5-6W at the output of the filter cube, under bright field illumination.

A typical failure analysis of a wafer level chip scale package includes pull testing. Such a process of pull testing can include, for example, a red dye pull test according to the following steps. To begin, the part under test is soaked in a mixture of organic solvent and red dye. The part under test is then removed from the mixture and allowed to dry. Subsequently, the part is subjected to either a shear or pull test, and tested to failure. After the shear or pull test, the process includes inspecting the part under bright light to verify if red dye has soaked into any failure point. Failure points can include one of a i.) solder crack, or ii.) delamination of epoxy to a die. However, contrast of the part under bright light is diminished, tending to render detail of the device under examination and the failure analysis less than optimal.

Another form of typical failure analysis includes bomb testing of hermetically sealed metal parts, such as TO-3 devices. The process of bomb testing includes, for example, a red dye bomb test according to the following steps. A capped part under test is placed into a pressurized vessel containing a red dye in an organic solvent. The vessel is pressurized to 100 psi and allowed to remain for 10-30 minutes. The pressure is then released and the part washed in acetone, for example, on the order of three times. Lastly, the part under test is decapped and inspected under bright field in search for dye that has ingressed into the device. However, contrast of the part under bright light is diminished, likewise rendering detail of the device under examination and the failure analysis less than optimal.

Accordingly, it would be desirable to provide an improved failure analysis that overcomes these and other problems in the art.

SUMMARY

According to one embodiment, a method for performing failure analysis on a semiconductor device under inspection includes preparing of a device sample using an encapsulation material containing a dye, the prepared device sample possibly including a failure area having wicked in encapsulation material containing the dye. The prepared device sample is then sectioned to facilitate viewing a cross section face of the device under inspection. Lastly, a dark field analysis on the prepared device sample is performed with the use of dark field illumination. Responsive to at least one failure area containing wicked in encapsulation material with dye occurring on the cross section face of the device under inspection, the failure area can be readily identified as well as a contrast and perspective of remaining portions of the cross section face being maintained.

BRIEF DESCRIPTION OF THE DRAWINGS

The embodiments of the present disclosure are illustrated by way of example and not limited by the accompanying figures, in which like references indicate similar elements, and in which.

DETAILED DESCRIPTION

Figure 1:
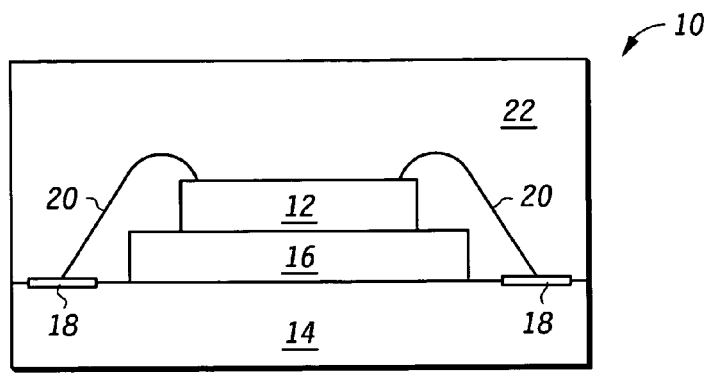
FIG. 1 is a schematic cross-sectional view of a wire bonded and assembled semiconductor device.

FIG. 1 is a schematic cross-sectional view of a typical wire bonded and assembled semiconductor device 10. Semiconductor device 10 includes a die 12 physically coupled to substrate 14 via a conventional die attach method such as die attach epoxy 16. In addition, device 10 includes die bond pads 18 disposed on substrate 14, wherein die wire bonds 20 interconnect between die 12 and substrate 14 at respective die bond pads. Furthermore, for performing a failure analysis on device 10, there is provided a mold compound 22 for encapsulating at least die 12, as well as other portions of device 10, as needed.

Figure 2:
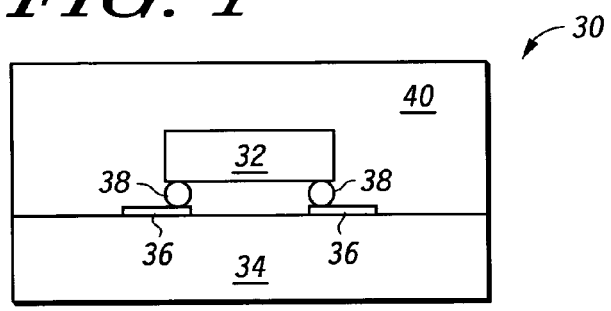
FIG. 2 is a schematic cross-sectional view of a flip chip assembled semiconductor device.

FIG. 2 is a schematic cross-sectional view of a flip chip assembled semiconductor device 30. Semiconductor device 30 includes a die 32 physically coupled to substrate 34 via a die attach pads 36 and solder spheres 38. That is, device 30 includes die attach bond pads 36 disposed on substrate 34, wherein the solder spheres 38 interconnect between die 32 and substrate 34 at respective die bond pads. For performing a failure analysis on device 30, there is provided a mold compound 40 for encapsulating at least die 32, as well as other portions of device 30, as needed.

Figure 3:
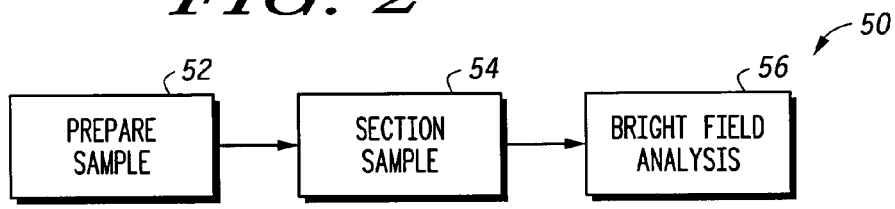
FIG. 3 is a flow diagram view of destructive testing with use of bright field analysis.

FIG. 3 is a flow diagram view of destructive testing 50 with use of bright field analysis. In the destructive testing flow diagram 50, the process begins with preparation of a device sample, that is, the device under analysis, as indicated by reference numeral 52. In step 54, the prepared sample is sectioned to facilitate viewing a cross-section face of the device under analysis. In step 56, a bright field analysis on the device under analysis is performed.

Figure 4:
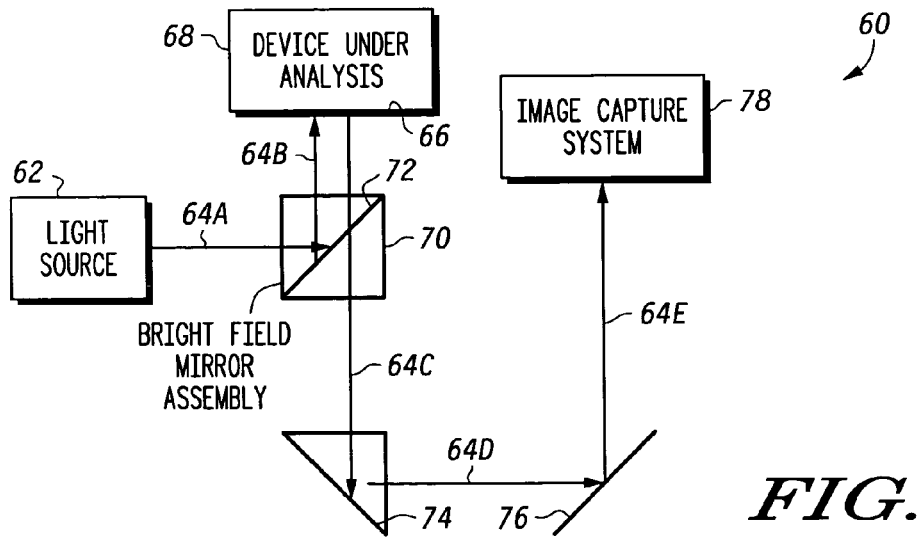
FIG. 4 is a plan view of a bright field illumination path for directly illuminating the face of a metallographic cross-section of a device under analysis.

FIG. 4 is a plan view of a failure analysis system 60 utilizing a light source 62 for producing a bright field illumination path 64. Bright field illumination path 64 directly illuminates a face 66 of a metallographic cross-section of a device under analysis 68. Light emanating from light source 62 is incident via path 64A upon bright field mirror assembly 70. Incident light via path 64A is reflected off of beam splitter 72 and directed via light path 64B towards the device under analysis 68. The light is then reflected off from the face 66 and returns via light path 64C through the bright field mirror assembly 70. System 60 contains additional mirror assemblies 74, 76, as well as an image capture system 78. Light along path 64C reflects off of mirror assembly 74 and is directed via path 64D to mirror assembly 76. Light reflected from mirror 76 is then directed via path 64E towards image capture system 78.

Figure 5:
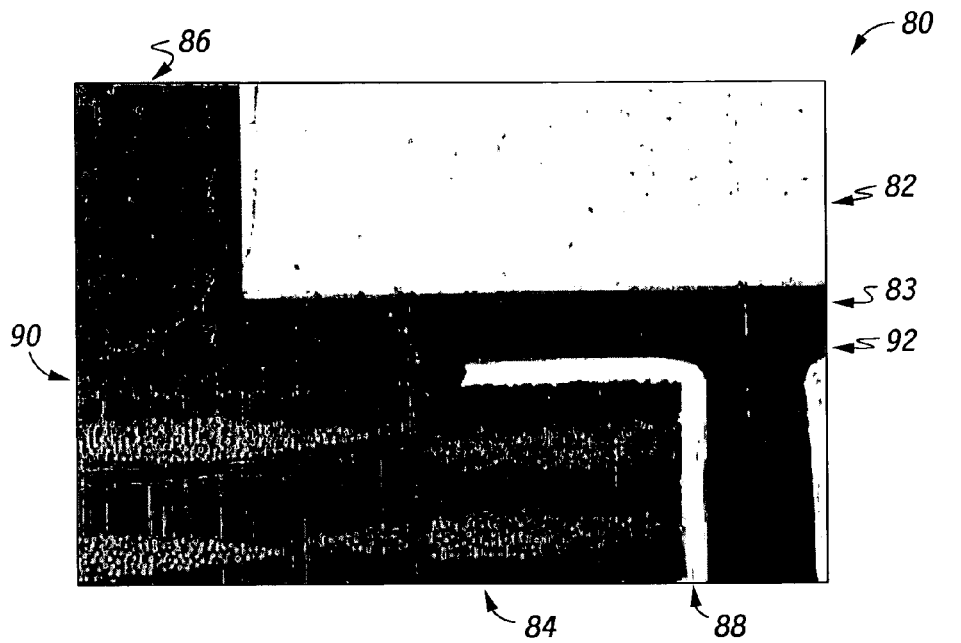
FIG. 5 is a metallographic cross-sectional view of a portion of a semiconductor device under bright field illumination at 100× amplification.

FIG. 5 is a metallographic cross-sectional view of a portion of a semiconductor device 80 under bright field illumination at 100× amplification using the system 60 of FIG. 4. FIG. 5 illustrates a portion of die 82 attached to underlying substrate 84. FIG. 5 further includes a portion of mold compound 86, a substrate interconnect 88, and a soldermask 90. From electrical testing, semiconductor device 80 was determined to be defected; however, a delaminated area was not readily observable under the bright field illumination from system 60 of FIG. 4.

Further with respect to the cross-sectional view of FIG. 5, components of the portion of the semiconductor device 80 show a limited amount of contrast, for example, between the silicon die 82, die attach epoxy 83, substrate 84, and mold compound 86. A lack of contrast and diminished detail is evident in that the delaminated area 92 between the substrate 84, mold compound 86 and die attach epoxy 83 is not clearly visible. This is a current issue when using cross-sectioning techniques in which there is little contrast between the various components and the cross section encapsulation material.

Figure 6:
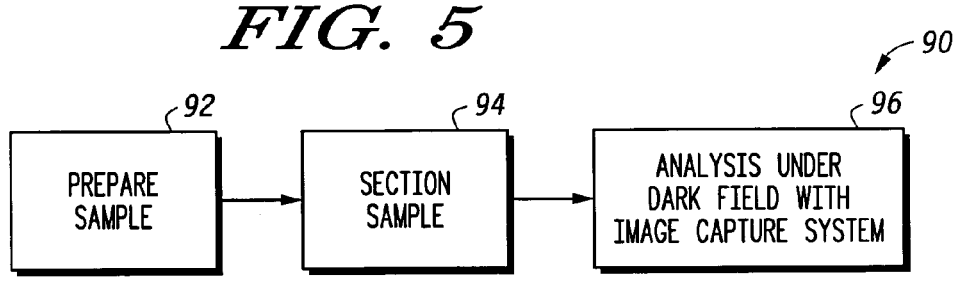
FIG. 6 is a flow diagram view of destructive testing enhanced with fluorescent dye testing and dark field analysis according to one embodiment of the present disclosure.

FIG. 6 is a flow diagram view of destructive testing 90 enhanced with fluorescent dye testing and dark field analysis according to one embodiment of the present disclosure. In the destructive testing flow diagram 90, the process begins with preparation of a device sample, that is, the device under analysis, as indicated by reference numeral 92. As part of the preparation of the sample in step 92, a dye is added to an uncured epoxy encapsulation material, the sample placed in a container along with the uncured epoxy containing the dye, and then the same is placed in a vacuum chamber and put under vacuum for a duration of time sufficient for allowing the dye, epoxy encapsulation material to be forced into any areas of delamination. In one embodiment, the encapsulant material includes a two component encapsulant, that is, a resin and a hardener. Accordingly, the conditions within the vacuum chamber allow the dye, cross section encapsulation material to be forced into any areas of delamination of the device under analysis.

After a vacuum purge cycle interval, the dye, cross section encapsulation material is allowed to return to standard ambient conditions and cure for the recommended cure period of the epoxy manufacturer. In one embodiment, the dye includes at least one selected from the group consisting of a Xanthane, Naphthalimide, Perylene, Courmarin, and Fluorescein based family.

During curing of the epoxy encapsulant, the curing conditions precipitate the wicking of the uncured epoxy containing fluorescent dye into any delaminations of the semiconductor device being analyzed. In step 94, the prepared sample is sectioned to facilitate viewing a cross-section face of the device under analysis. Sectioning of the sample can include rough grinding, fine grinding, and then polishing, prior to subjecting the sample to dark field inspection.

In step 96, a dark field analysis with image capture is performed on the device under analysis. Dark field analysis can be accomplished with the use of a compound microscope configured for dark field illumination and having a typical image capture system attached for capturing images of the device under analysis, such as digital images. The dark field analysis includes the use of dark field illumination. Under dark field illumination, a full complement of light is available for illumination of the device under analysis, at an angle different than bright field. In other words, with the dark field illumination, the light input is substantially the same as the light output.

According to one embodiment, the fluorescent dye includes a xanthene based fluorescent dye. Xanthene based dye pigments dissolve easily in potting media. Potting media include, for example, any clear, non-shrinking, 2 component epoxy encapsulant system that provides structural support during the cross sectioning process. As opposed to other types of fluorescent dyes, such other types of fluorescent dyes require a pre-dissolving step, for example, using ethanol. Such a pre-dissolving step undesirably yields a long cure time.

As noted above, with xanthene based dyes, there is no interaction between the dye and the potting media. Xanthene based dyes are also generally less costly, as compared to other dyes. In addition, it has been observed that there is no UV degradation of an encapsulated xanthene based dye with time. Furthermore, the dye is able to withstand high temperatures on the order of above 150 degrees Celsius, is opaque, has a small particle size on the order of approximately 3-5 µm diameter or smaller, and is readily visible under dark field illumination. Pigment size is critical, as larger size pigments will not sufficiently wick into small areas of delamination.

A study of various dyes was conducted for accessing emission and excitation qualities of the same, the dyes including saffarine, rhodamine 6G, 1,8 diazofluoren-9-One, and Xanthene. For each dye of the study, the excitation filter that was used included a 568 nm filter. The emission filter included a 610 nm filter. As evidenced in Table 1 below, of the four dyes, all provided acceptable results, except 1,8 diazofluoren-9-One. Results are based on dye or color being visually present under either bright or dark field inspection. In particular, under dark field illumination, with the Xanthene dye, delaminated areas of the device under test become detectable, that is, visible. Under dark field illumination, however, the other dyes fail to provide sufficient visibility to any delaminated areas of the device part under test.

TABLE 1

| | Excitation Filter | Emission Filter | Results | Dark-field |
|---|---|---|---|---|
| Saffarine | 568 nm | 610 nm | Acceptable | No |
| Rhodamine 6G | 568 nm | 610 nm | Acceptable | No |
| 1,8 Diazofluoren-9-One | 568 nm | 610 nm | Not Acceptable | No |
| Xanthene | 568 nm | 610 nnm | Acceptable | Yes |

Figure 7:
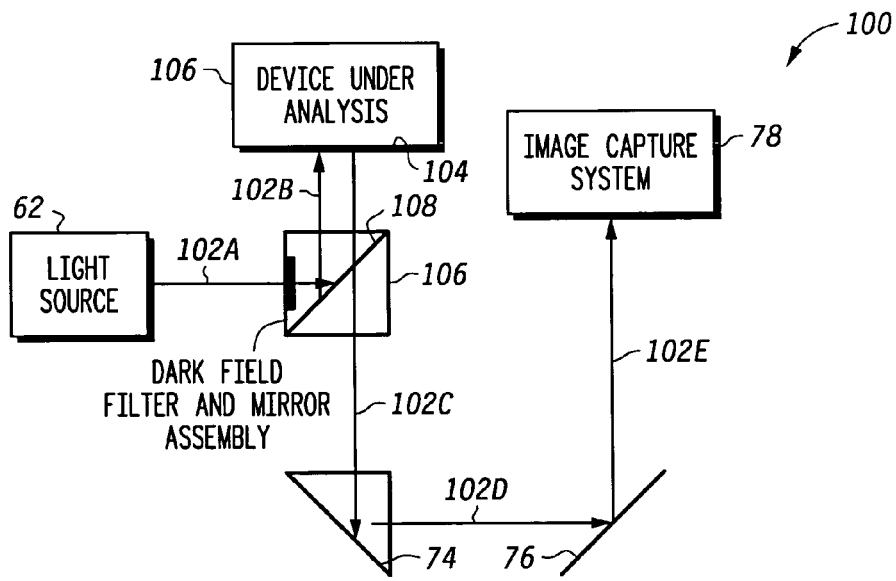
FIG. 7 is a plan view of a dark field illumination path for illuminating the sides of the metallographic cross-section of the device under analysis.

Turning now to FIG. 7, a plan view of a failure analysis system 100 is shown that utilizes a light source 62 for producing a dark field illumination path 102 and for illuminating the sides of face 104 of the metallographic cross-section of the device under analysis. Dark field illumination path 102 indirectly illuminates a face 104 of the metallographic cross-section of the device under analysis 106. Light emanating from light source 62 is incident via path 102A upon dark field filter and mirror assembly 106. Incident light via path 102A is reflected off of beam splitter 108 and directed via light path 102B towards the device under analysis 106. The light is then reflected off from the face 104 of the device under analysis and returns via light path 102C through the dark field filter mirror assembly 106.

System 100 contains additional mirror assemblies 74, 76, as well as an image capture system 78. Light along path 102C reflects off of mirror assembly 74 and is directed via path 102D to mirror assembly 76. Light reflected from mirror 76 is then directed via path 102E towards image capture system 78. Under dark field illumination, contrast of the features being viewed is maintained, as well as, providing an ability to identify locations where the fluorescent dye resides in the device under analysis. In one embodiment, the feature size may range from on the order of 25 µm with a magnification on-the order of 100-200× to a feature size on the order of less than 1 µm with a magnification on the order of 1000×.

Figure 8:
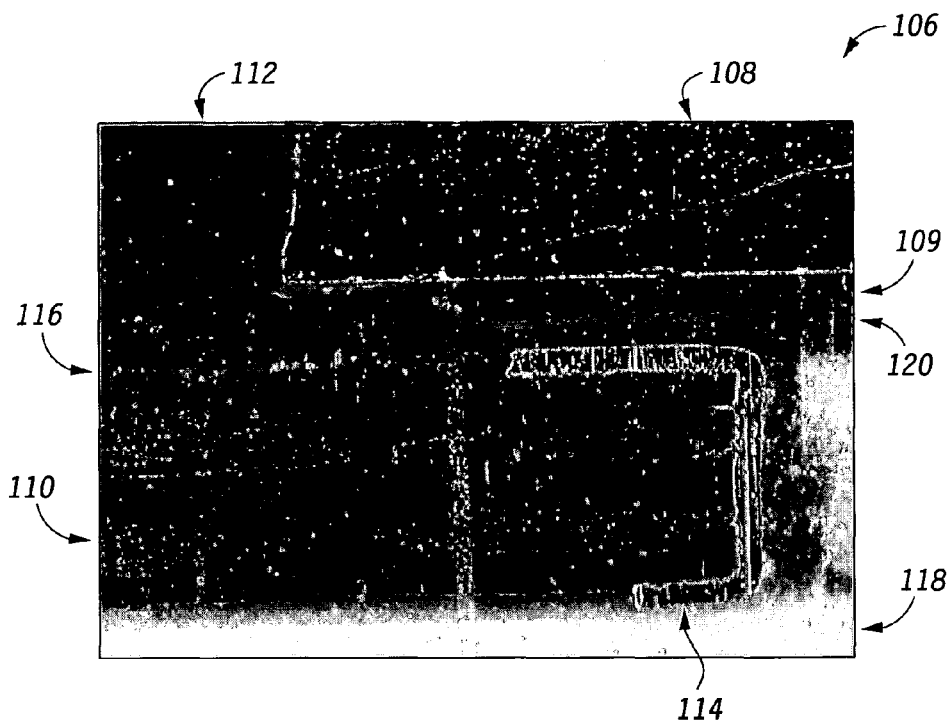
FIG. 8 is a metallographic cross-sectional view of a portion of a semiconductor device under dark field illumination at 100× amplification.

FIG. 8 is a metallographic cross-sectional view of a portion of a semiconductor device 106 under dark field illumination at 100× amplification using the system 100 of FIG. 7. FIG. 8 illustrates a portion of die 108 attached with die attach epoxy 109 to an underlying substrate 110. FIG. 8 further includes a portion of mold compound 112, a substrate interconnect 114, and a soldermask 116. From electrical testing, for example, semiconductor device 106 was determined to be defected.

Using the method of failure analysis according to one embodiment of the present disclosure, including the combination of the use of dark field illumination and the incorporation of fluorescent dye into the encapsulation material 118 for the device under analysis, it is possible to search for and observe a delaminated area 120 under the dark field illumination from system 100 of FIG. 7. That is, when viewed under dark field illumination after fluorescent dye has been incorporated into the encapsulation material, the contrast provided by the combination of dark field illumination and use of the fluorescent dye clearly shows, and makes readily visible, the delamination area 120 between the substrate, mold compound and die attach epoxy, while also providing substantially no diminished areas of contrast of the remaining portions or components of the semiconductor device cross-section.

Figure 9:
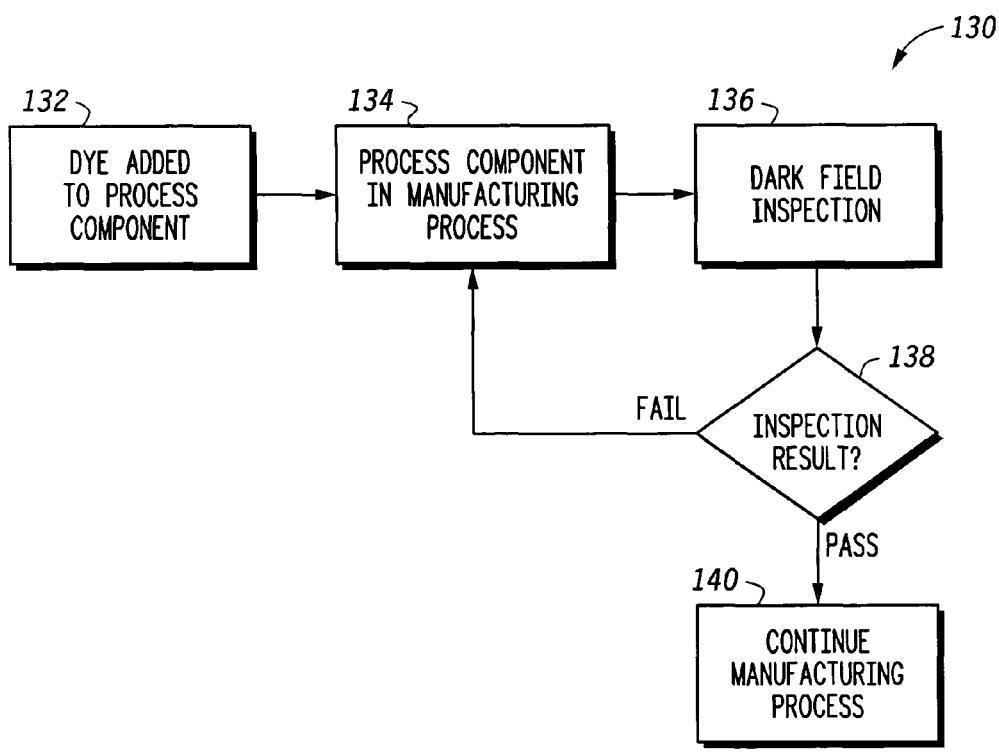
FIG. 9 is a flow diagram view of non-destructive testing with fluorescent dye and dark field analysis according to another embodiment of the present disclosure.

FIG. 9 is a flow diagram view of non-destructive testing 130 with fluorescent dye and dark field analysis according to another embodiment of the present disclosure. In the non-destructive testing flow diagram 130, the process begins with the addition of dye to a process component, as indicated by reference numeral 132. As noted earlier herein, the dye can include at least one selected from the group consisting of a Xanthane, Naphthalimide, Perylene, Courmarin, and Fluorescein based family. The process component can include, for example, at least one selected from the group consisting of a photo resist, a solder mask, BCB, flux, and an organic passivation layer. Accordingly, the dye can be added to any process component used in either a semiconductor or printed circuit board manufacturing industry.

The process component is then processed through manufacturing processing typical for such process component, as indicated by reference numeral 134. After processing of the process component, the device under manufacture is then inspected under dark field illumination as indicated by reference numeral 136. Inspection under dark field illumination serves to verify a presence or absence of dye on a particular area of the device under manufacture and/or the process component, such as a bond pads or unwanted areas. For example, one embodiment may include determining whether a residue of material on the order of several angstroms has been removed.

At step 138, a query is conducted regarding the inspection results. If the inspection results indicate a failure of a desired outcome, for example, the continued presence or absence of dye on a particular area, then the process returns to the step of processing the process component at 134. If the inspection results indicate achievement of the desired outcome, then the inspection passes and the process proceeds at step 140 with a continuation of the manufacturing process for the device under manufacture. Accordingly, a decision is made whether or not to continue the manufacturing process of the device under manufacture. Alternatively, subsequent to the processing step at 134, the dye in the process component may be removed, if required, and the device under manufacture continues to a next processing step in the manufacturing process, as indicated by reference numeral 140.

According to another embodiment, a method of performing failure analysis includes using inexpensive fluorescent inks in combination with industry practiced cross-sectioning techniques. Accordingly, points of failure in a region of a device under inspection are easily determined with the correct emission/excitation filters, or with dark field microscope inspection, without losing the contrast of a remainder of the device under inspection. In one embodiment, the fluorescent inks include inks belonging to the xanthene class.

According to yet another embodiment, the method and system apparatus uses low cost fluorescent inks with the correct emission/excitations filter or with standard dark field illumination techniques to determine the point of failure. Most inks or dyes under existing fluorescent microscope inspection loose contrast between the fluorescing dye and the remainder of the device under inspection. In general bright field provides acceptable illumination but with poor contrast, filter cubes provide poor illumination and poor contrast, while dark field provides excellent illumination and excellent contrast.

Moreover, the method of the present disclosure can be applied to failure analysis of a variety of devices. Such devices can include, for example, a wide variety of packages such as flip chip assembly (FCA), QFN assembly, wafer level chip scale packages (WL-CSP), and chip on board assembled product.

The method of failure analysis using fluorescent dye under dark field inspection requires no specialized filters. Furthermore, the method of failure analysis using fluorescent dye under dark field inspection can operate with standard light sources, for example, on the order of 100 W-150 W. Lastly, the method of failure analysis using fluorescent dye under dark field inspection provides enhanced contrast between a failed area and a remaining section of the device under inspection.

In an improved failure analysis via pull testing according to one embodiment of the present disclosure, the process includes a fluorescent dye pull test. For example, the process includes the following steps. First, the method includes soaking the part under test in a mixture of organic solvent with a fluorescent dye that is strongly visible under dark field illumination. Next, the process includes removing the part under test from the mixture and allowing the part to dry. Subsequently, the part is subjected to either a shear or pull test, and tested to failure. Lastly, the process includes inspecting the part under dark field illumination to verify if any red dye has soaked into any failure point. Failure points include at least one of the group consisting of: i.) a solder crack and ii.) delamination of epoxy to die.

In another embodiment of present disclosure, an improved failure analysis process via bomb testing includes a fluorescent dye bomb test of hermetically sealed metal parts, such as TO-3 devices. In particular, the process includes the following steps. A capped device under test is placed into a pressurized vessel containing a fluorescent dye that is strongly visible under dark field illumination in an organic solvent. The vessel is pressurized to 100 psi and allowed to remain for 10-30 minutes. The pressure is then released. Lastly, the device under test is mechanically decapped and inspected under dark field illumination in search for fluorescent dye that has ingressed into the device.

In the foregoing specification, the disclosure has been described with reference to various embodiments. However, one of ordinary skill in the art appreciates that various modifications and changes can be made without departing from the scope of the present embodiments as set forth in the claims below. Accordingly, the specification and figures are to be regarded in an illustrative rather than a restrictive sense, and all such modifications are intended to be included within the scope of the present embodiments.

Benefits, other advantages, and solutions to problems have been described above with regard to specific embodiments. However, the benefits, advantages, solutions to problems, and any element(s) that may cause any benefit, advantage, or solution to occur or become more pronounced are not to be construed as a critical, required, or essential feature or element of any or all the claims. As used herein, the term "comprises," "comprising," or any other variation thereof, are intended to cover a non-exclusive inclusion, such that a process, method, article, or apparatus that comprises a list of elements does not include only those elements by may include other elements not expressly listed or inherent to such process, method, article, or apparatus.

The invention claimed is:

1. A method for performing failure analysis on a semiconductor device under inspection, comprising:
preparing of a sample of the semiconductor device under inspection using an encapsulation material containing a dye, the prepared device sample possibly including at least one failure area containing wicked in encapsulation material containing the dye;
sectioning the prepared device sample to facilitate viewing a cross section face of the device under inspection;
performing a dark field analysis on the prepared device sample with the use of dark field illumination, wherein responsive to at least one failure area containing wicked in encapsulation material with dye occurring on the cross section face of the device under inspection, the failure area can be readily identified as well as a contrast and perspective of remaining portions of the cross section face being maintained; and
repeating the sectioning of the prepared device sample to facilitate viewing another cross-section face of the device under inspection, and performing dark field analysis on the another cross section face of the prepared device sample with the use of dark field illumination.

2. The method of claim 1, wherein the semiconductor device includes a wafer level chip scale packaged semiconductor device.

3. The method of claim 1, wherein the dye includes at least one fluorescent dye selected from the group consisting of a Xanthane, Naphthalimide, Perylene, Courmarin, and Fluorescein based family.

4. The method of claim 1, wherein the dye includes a dye pigment that is added to an uncured epoxy encapsulation material.

5. The method of claim 4, wherein preparing the device sample further includes placing the sample into a container along with the uncured epoxy containing the dye pigment, placing the same in a vacuum chamber, and maintaining the same under vacuum within the vacuum chamber for a duration of time sufficient for allowing the uncured epoxy encapsulation material containing dye to wick into a failure area of delamination extending from an exterior to an interior of the device sample.

6. The method of claim 5, further including configuring the conditions within the vacuum chamber to promote wicking of the encapsulation material containing dye into the failure area.

7. The method of claim 5, wherein preparing the device sample further includes employing a vacuum purge cycle subsequent to placing the device sample under vacuum within the vacuum chamber for the duration of wicking, allowing the dye and encapsulation material to return to standard ambient conditions, and then curing the encapsulation material containing the dye.

8. The method of claim 4, further wherein the encapsulation material includes a two component encapsulant comprised of a resin and a hardener.

9. The method of claim 1, wherein sectioning of the sample includes rough grinding, followed by fine grinding, and then polishing, prior to subjecting the sample to the dark field analysis.

10. The method of claim 1, wherein performing the dark field analysis includes capturing an image of the cross section of the prepared device sample under dark field illumination.

11. The method of claim 1, further wherein performing the dark field analysis includes using a compound microscope configured for dark field illumination and inspection and wherein the compound microscope includes an image capture system coupled to the compound microscope for capturing an image of the cross section face of the device under inspection.

12. The method of claim 11, wherein the captured image include a digital image.

13. The method of claim 1, wherein the dark field illumination includes use of a full complement of light for illuminating the cross section face of the device under inspection.

14. A method for performing failure analysis on a semiconductor device under inspection, comprising:
preparing of a sample of the semiconductor device under inspection using an encapsulation material containing a dye, the prepared device sample possibly including at least one failure area containing wicked in encapsulation material containing the dye;
sectioning the prepared device sample to facilitate viewing a cross section face of the device under inspection;

performing a dark field analysis on the prepared device sample with the use of dark field illumination, wherein responsive to at least one failure area containing wicked in encapsulation material with dye occurring on the cross section face of the device under inspection, the failure area can be readily identified as well as a contrast and perspective of remaining portions of the cross section face being maintained; and prior to preparing and sectioning the device sample, performing an initial assessment of the device under inspection with the use of acoustic scanning to determine a location for cross sectioning the device sample, the location corresponding to a potential failure area or point of delamination in the device sample.

15. A method of manufacturing a semiconductor device comprising:
    fabricating the semiconductor device;
    performing a failure analysis on the semiconductor device, the failure analysis including
    (a) preparing of a sample of the semiconductor device under inspection using an encapsulation material containing a dye, the prepared device sample possibly including at least one failure area containing wicked in encapsulation material containing the dye, (b) sectioning the prepared device sample to facilitate viewing a cross section face of the device under inspection, and (c) performing a dark field analysis on the prepared device sample with the use of dark field illumination, wherein responsive to at least one failure area containing wicked in encapsulation material with dye occurring on the cross section face of the device under inspection, the failure area can be readily identified as well as a contrast and perspective of remaining portions of the cross section face being maintained;
    adjusting the manufacturing process in response to an outcome of the failure analysis; and
    repeating the sectioning of the prepared device sample to facilitate viewing another cross-section face of the device under inspection, and performing dark field analysis on the another cross section face of the prepared device sample with the use of dark field illumination.

16. The method of claim 15, wherein the semiconductor device includes a wafer level chip scale packaged semiconductor device.

17. The method of claim 15, wherein the dye includes at least one fluorescent dye selected from the group consisting of a Xanthane, Naphthalimide, Perylene, Courmarin, and Fluorescein based family.

18. The method of claim 15, wherein the dye includes a dye pigment that is added to an uncured epoxy encapsulation material.

19. The method of claim 18, wherein preparing the device sample further includes placing the sample into a container along with the uncured epoxy containing the dye pigment, placing the same in a vacuum chamber, and maintaining the same under vacuum within the vacuum chamber for a duration of time sufficient for allowing the uncured epoxy encapsulation material containing dye to wick into a failure area of delamination extending from an exterior to an interior of the device sample.

20. The method of claim 15, further wherein performing the dark field analysis includes using a compound microscope configured for dark field illumination and inspection and wherein the compound microscope includes an image capture system coupled to the compound microscope for capturing an image of the cross section face of the device under inspection.

21. The method of claim 15, further comprising:
    prior to preparing and sectioning the device sample, performing an initial assessment of the device under inspection with the use of acoustic scanning to determine a location for cross sectioning the device sample, the location corresponding to a potential failure area or point of delamination in the device sample.

* * * * *